United States Patent
Tanaka et al.

(10) Patent No.: US 8,796,461 B2
(45) Date of Patent: Aug. 5, 2014

(54) 1,2,4,5-SUBSTITUTED PHENYL COMPOUND, METHOD FOR PRODUCING SAME AND ORGANIC ELECTROLUMINESCENT DEVICE COMPRISING SAME AS CONSTITUENT

(75) Inventors: Tsuyoshi Tanaka, Ayase (JP); Mayumi Abe, Ayase (JP); Nobumichi Arai, Ayase (JP); Naoki Uchida, Ayase (JP); Takashi Iida, Ayase (JP)

(73) Assignee: Tosoh Corporation, Yamaguchi (JP)

( * ) Notice: Subject to any disclaimer, the term of this patent is extended or adjusted under 35 U.S.C. 154(b) by 0 days.

(21) Appl. No.: 13/634,943

(22) PCT Filed: Mar. 16, 2011

(86) PCT No.: PCT/JP2011/056190
§ 371 (c)(1),
(2), (4) Date: Oct. 22, 2012

(87) PCT Pub. No.: WO2011/115163
PCT Pub. Date: Sep. 22, 2011

(65) Prior Publication Data
US 2013/0035491 A1    Feb. 7, 2013

(30) Foreign Application Priority Data

Mar. 16, 2010  (JP) .................................. 2010-059889
Dec. 16, 2010  (JP) .................................. 2010-280818

(51) Int. Cl.
C07D 213/04    (2006.01)
C07D 213/06    (2006.01)

(52) U.S. Cl.
CPC .................................. *C07D 213/06* (2013.01)
USPC ...................................................... 546/255

(58) Field of Classification Search
None
See application file for complete search history.

(56) References Cited

U.S. PATENT DOCUMENTS

| | | | |
|---|---|---|---|
| 6,852,249 B2 * | 2/2005 | Lu et al. .................. | 252/301.16 |
| 7,994,316 B2 | 8/2011 | Yamakawa et al. | |
| 8,268,997 B2 | 9/2012 | Yamakawa et al. | |
| 2001/0021478 A1 | 9/2001 | Shi et al. | |
| 2001/0023029 A1 | 9/2001 | Shi et al. | |
| 2003/0166920 A1 | 9/2003 | Lu et al. | |
| 2009/0072715 A1 | 3/2009 | Suzuri et al. | |
| 2010/0308313 A1 | 12/2010 | Yamaguchi et al. | |
| 2011/0001129 A1 | 1/2011 | Yokoyama et al. | |
| 2011/0190494 A1 | 8/2011 | Aihara et al. | |
| 2011/0288295 A1 | 11/2011 | Aihara et al. | |
| 2012/0161107 A1 | 6/2012 | Yokoyama et al. | |
| 2012/0214993 A1 | 8/2012 | Aihara et al. | |

FOREIGN PATENT DOCUMENTS

| | | |
|---|---|---|
| CN | 101654430 A | 2/2010 |
| EP | 1009043 | 6/2000 |
| JP | 2003-336043 | 11/2003 |
| JP | 2005-255986 | 9/2005 |
| JP | 2007-015993 | 1/2007 |
| JP | 2008-63232 | 3/2008 |
| JP | 2008-127326 | 6/2008 |
| JP | 2010-90085 | 4/2010 |
| WO | 2006/103909 | 10/2006 |
| WO | 2009/081873 | 7/2009 |
| WO | 2009/107651 | 9/2009 |
| WO | 2009/151039 | 12/2009 |

OTHER PUBLICATIONS

U.S. Appl. No. 13/590,837 to Tetsu Yamakawa et al., filed Aug. 21, 2012.
Search report from International Application No. PCT/JP2011/056190, mail date is Jun. 21, 2011.
Extended European Search Report in EP 11756347.8 dated Jun. 20, 2013.
Zhong Hui Li et al., "Novel fluorine-containing X-branched oligophenylenes: structure-hole blocking property relationships", Journal of Materials Chemistry, 2006, vol. 16, Dec. 14, 2005, pp. 765-772.

* cited by examiner

*Primary Examiner* — Heidi Reese
(74) *Attorney, Agent, or Firm* — Greenblum & Bernstein, P.L.C.

(57) ABSTRACT

A 1,2,4,5-substituted phenyl compound represented by the formula (1):

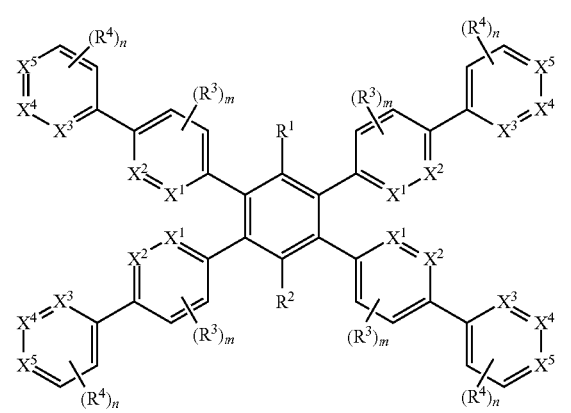

(1)

wherein one of $X^1$-$X^5$ is nitrogen and the remainders of $X^1$-$X^5$ are carbon; $R^1$ and $R^2$ represent hydrogen, $C_{1-6}$ alkyl or $C_{1-6}$ alkoxy; $R^3$ and $R^4$ represent $C_{1-6}$ alkyl or $C_{1-6}$ alkoxy; and m is an integer of 0-4, and n is an integer of 0-5. This compound is useful as a constituent for an organic electroluminescent device.

3 Claims, 1 Drawing Sheet

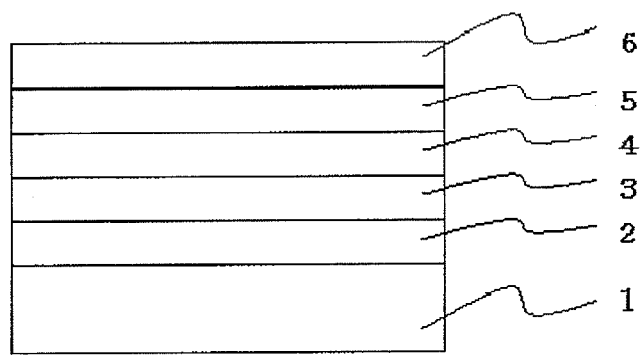

1,2,4,5-SUBSTITUTED PHENYL COMPOUND, METHOD FOR PRODUCING SAME AND ORGANIC ELECTROLUMINESCENT DEVICE COMPRISING SAME AS CONSTITUENT

TECHNICAL FIELD

This invention relates to a 1,2,4,5-substituted phenyl compound, a process for preparing the same, and an organic electroluminescent device comprising the same as a constituent.

The 1,2,4,5-substituted phenyl compound of the present invention exhibits good charge-transporting property and forms a stable thin film, therefore, is useful as a component of a fluorescent or phosphorescent organic electroluminescent device.

Thus, this invention further relates to an organic electroluminescent device having at least one organic compound layer containing the 1,2,4,5-substituted phenyl compound as a constituent, which is a highly efficient organic electroluminescent device exhibiting improved drivability and light emission characteristics.

BACKGROUND ART

An organic electroluminescent (EL) device has a multilayer structure comprising (i) a luminescent layer comprising a light emitting material and (ii) a hole transport layer and an electron transport layer, which sandwich the luminescent layer, and (iii) an anode and a cathode, which sandwich the hole transport layer, the luminescent layer and the electron transport layer. The organic EL device utilizes light emission (fluorescence or phosphorescence) occurring at deactivation of an exciton formed by the recombination of electron with hole, which are injected in the luminescent layer. The organic EL device is widely used for a display and other applications.

The organic EL device is utilized in various display instruments. For utilization thereof for personal digital assistants to which supply of an electric power is restricted, it is required or eagerly desired that the power consumption is further lowered. Simultaneously, for the commercial utilization of the organic EL device, it is important to prolong the life of device with stable performances.

The 1,2,4,5-substituted phenyl compound of the present invention is characterized as having a pyridyl-substituted phenlylene group or a phenyl-substituted pyridylene group at each of 1, 2, 4 and 5 positions of a benzene ring.

Recently it has been proposed to utilize a compound having an aromatic cyclic hydrocarbon group having introduced therein bipyridyl groups, as a 1,2,4,5-substituted phenyl compound for an organic EL device in, for example, WO2009/151039. However, this patent publication is silent on a compound having pyridyl-substituted phenlylene groups or phenyl-substituted pyridylene groups on a benzene ring.

Further, it has been proposed to utilize a 1,2,4,5-substituted oligophenylene compound for an organic EL device in, for example, WO2009/081873. However, this patent publication is silent on a compound having pyridyl-substituted phenlylene groups or phenyl-substituted pyridylene groups, which are bonded to a benzene ring. Enhancement of light emission efficiency of the substituted oligophenylene compound is discussed in WO2009/081873, but, lowering of the power consumption and prolongation of the life of device are not mentioned therein.

Further, compounds having combinations of a phenyl group with a pyridyl group for use in an organic EL device have been proposed in, for example, JP2008-63232A, JP2003-336043, JP2007-015993A, JP2005-255986A and JP2008-127326A. However, these patent publications are silent on a compound having pyridyl-substituted phenlylene groups or phenyl-substituted pyridylene groups, which are bonded to a benzene ring. Organic EL devices made by using the compounds proposed in these patent publications still do not have sufficiently improved luminescent characteristics.

SUMMARY OF THE INVENTION

Problems to be Solved by the Invention

A primary object of the present invention is to provide a novel 1,2,4,5-substituted phenyl compound giving an organic EL device exhibiting improved low-voltage drivability and enhanced durability and life, when the compound is used as a constituent of the organic EL device.

Another object of the present invention is to provide a process for preparing the 1,2,4,5-substituted phenyl compound in an industrially advantageous manner.

A further object of the present invention is to provide an organic EL device exhibiting improved low-voltage drivability, and enhanced durability and life.

To solve the above-mentioned problems, the present inventors made an extensive research and found that the 1,2,4,5-substituted phenyl compound of the present invention can be made into a thin film by a conventional method such as vacuum deposition, and further that an organic EL device having an electron transport layer comprised of the 1,2,4,5-substituted phenyl compound exhibits a reduced power consumption and prolonged life as compared with the organic EL devices widely used. Based on these findings, the present invention has been completed.

In one aspect of the present invention, there is provided a 1,2,4,5-substituted phenyl compound represented by the following formula (1):

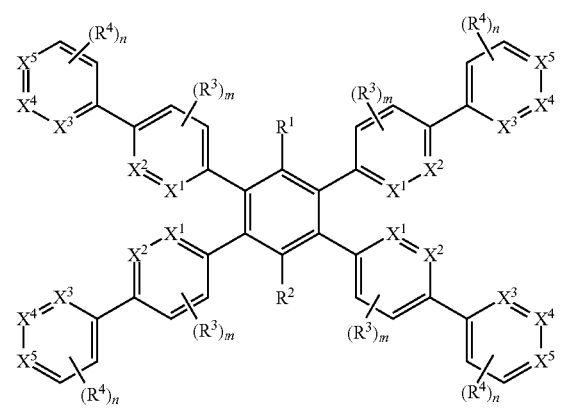

(1)

In the formula (1), one of $X^1$ through $X^5$ represents a nitrogen atom and the remainders of $X^1$ through $X^5$ represent a carbon atom. $R^1$ and $R^2$ independently represent a hydrogen atom, an alkyl group having 1 to 6 carbon atoms or an alkoxy group having 1 to 6 carbon atoms. $R^3$ and $R^4$ independently represent an alkyl group having 1 to 6 carbon atoms or an alkoxy group having 1 to 6 carbon atoms. m represents an integer in the range of 0 to 4, provided that, in the case when m is at least 2, each $R^3$ may be the same or different. n represents an integer in the range of 0 to 5, provided that, in the case when n is at least 2, each $R^4$ may be the same or different.

In another aspect of the present invention, there is provided a process (first process) for preparing a 1,2,4,5-substituted phenyl compound represented by the following formula (1):

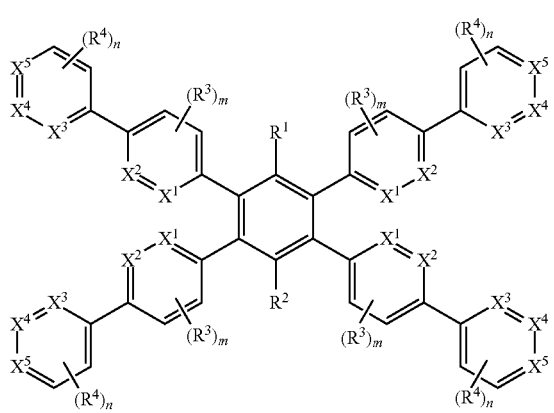

(1)

In the formula (1), one of $X^1$ through $X^5$ represents a nitrogen atom and the remainders of $X^1$ through $X^5$ represent a carbon atom. $R^1$ and $R^2$ independently represent a hydrogen atom, an alkyl group having 1 to 6 carbon atoms or an alkoxy group having 1 to 6 carbon atoms. $R^3$ and $R^4$ independently represent an alkyl group having 1 to 6 carbon atoms or an alkoxy group having 1 to 6 carbon atoms. m represents an integer in the range of 0 to 4, provided that, in the case when m is at least 2, each $R^3$ may be the same or different. n represents an integer in the range of 0 to 5, provided that, in the case when n is at least 2, each $R^4$ may be the same or different.

The above-mentioned first process is characterized by comprising a step of subjecting a compound represented by the following formula (2) to a coupling reaction with a compound represented by the following formula (3) in the presence of a base and a metal catalyst.

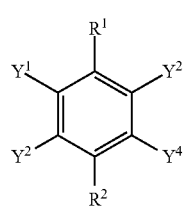

(2)

In the formula (2), $Y^1$ through $Y^4$ independently represent a leaving group, $R^1$ and $R^2$ independently represent a hydrogen atom, an alkyl group having 1 to 6 carbon atoms or an alkoxy group having 1 to 6 carbon atoms.

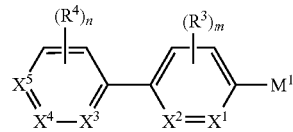

(3)

In the formula (3), one of $X^1$ through $X^5$ represents a nitrogen atom and the remainders of $X^1$ through $X^5$ represent a carbon atom. $R^3$ and $R^4$ independently represent an alkyl group having 1 to 6 carbon atoms or an alkoxy group having 1 to 6 carbon atoms. m represents an integer in the range of 0 to 4, provided that, in the case when m is at least 2, each $R^3$ may be the same or different. n presents an integer in the range of 0 to 5, provided that, in the case when n is at least 2, each $R^4$ may be the same or different. $M^1$ represents a metallic group or a heteroatom group.

In a further aspect of the present invention, there is provided a process (second process) for preparing a 1,2,4,5-substituted phenyl compound represented by the following formula (1):

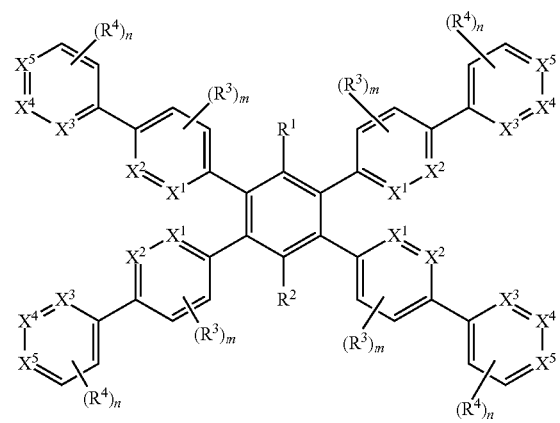

(1)

In the formula (1), one of $X^1$ through $X^5$ represents a nitrogen atom and the remainders of $X^1$ through $X^5$ represent a carbon atom. $R^1$ and $R^2$ independently represent a hydrogen atom, an alkyl group having 1 to 6 carbon atoms or an alkoxy group having 1 to 6 carbon atoms. $R^3$ and $R^4$ independently represent an alkyl group having 1 to 6 carbon atoms or an alkoxy group having 1 to 6 carbon atoms. m represents an integer in the range of 0 to 4, provided that, in the case when m is at least 2, each $R^3$ may be the same or different. n represents an integer in the range of 0 to 5, provided that, in the case when n is at least 2, each $R^4$ may be the same or different.

The above-mentioned second process is characterized by comprising a step of subjecting a compound represented by the following formula (4) to a coupling reaction with a compound represented by the following formula (5) in the presence of a base and a metal catalyst.

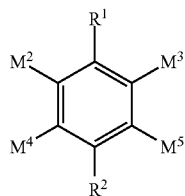

(4)

In the formula (4), $R^1$ and $R^2$ independently represent a hydrogen atom, an alkyl group having 1 to 6 carbon atoms or an alkoxy group having 1 to 6 carbon atoms. $M^2$ through $M^5$ independently represent a metallic group or a heteroatom group.

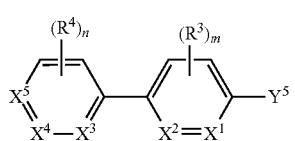

(5)

In the formula (5), one of $X^1$ through $X^5$ represents a nitrogen atom and the remainders of $X^1$ through $X^5$ represent a carbon atom. $R^3$ and $R^4$ independently represent an alkyl group having 1 to 6 carbon atoms or an alkoxy group having 1 to 6 carbon atoms. m represents an integer in the range of 0 to 4, provided that, in the case when m is at least 2, each $R^3$ may be the same or different. n represents an integer in the range of 0 to 5, provided that, in the case when n is at least 2, each $R^4$ may be the same or different. $Y^5$ represents a leaving group.

In a further aspect of the present invention, there is provided an organic electroluminescent device comprising as a constituent a 1,2,4,5-substituted phenyl compound represented by the following formula (1):

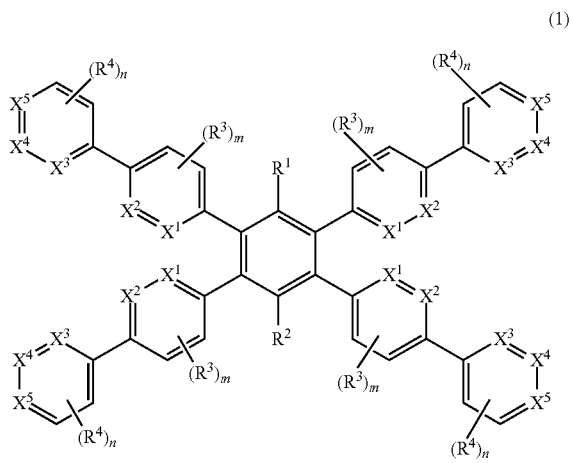

(1)

In the formula (1), one of $X^1$ through $X^5$ represents a nitrogen atom and the remainders of $X^1$ through $X^5$ represent a carbon atom. $R^1$ and $R^2$ independently represent a hydrogen atom, an alkyl group having 1 to 6 carbon atoms or an alkoxy group having 1 to 6 carbon atoms. $R^3$ and $R^4$ independently represent an alkyl group having 1 to 6 carbon atoms or an alkoxy group having 1 to 6 carbon atoms. m represents an integer in the range of 0 to 4, provided that, in the case when m is at least 2, each $R^3$ may be the same or different. n represents an integer in the range of 0 to 5, provided that, in the case when n is at least 2, each $R^4$ may be the same or different.

Effect of the Invention

A 1,2,4,5-substituted phenyl compound of the present invention represented by the formula (1) (hereinafter referred to as "compound (1)" when appropriate) gives a thin film having good charge injection characteristics and good charge transport characteristics. Therefore, the compound (1) is useful as a material, especially a host material, an electron transport material and other materials, for an organic fluorescent or phosphorescent EL device The compound (1) exhibits a bandgap of at least 3.2 eV, and a wide bandgap capable of sufficiently confining trichromatic energies of red: 1.9 eV, green: 2.4 eV, and blue: 2.8 eV constituting a panel. Therefore, the compound of the formula (1) can be used as a wide bandgap material for various devices such as a monochromatic display device, a trichromatic display device and a white light emitting device.

Solubility of the compound (1) can be controlled by varying substituents thereof, therefore, the compound can also be applied to a coated device as well as a vacuum deposited device.

Thus, a fluorescent or phosphorescent organic EL device comprising the compound (1) exhibits improved low-voltage drivability and enhanced durability and life, as compared with organic EL devices comprising the conventional fluorescent or phosphorescent materials.

BRIEF DESCRIPTION OF THE DRAWINGS

FIG. 1 illustrates a schematic cross-section of an example of an organic EL device having a thin film layer comprised of the compound (1) of the present invention.

EXPLANATION OF REFERENCE NUMERALS

1. Glass substrate with transparent ITO electrode
2. Hole injection layer
3. Hole transport layer
4. Light emitting layer
5. Electron transport layer
6. Cathode layer

BEST MODE FOR CARRYING OUT THE INVENTION

The invention will now be described in detail.

In the formula (1) for the 1,2,4,5-substituted phenyl compound of the present invention, one of $X^1$ through $X^5$ represents a nitrogen atom and the remainders of $X^1$ through $X^5$ represent a carbon atom. It is impossible that two or more of $X^1$ through $X^5$ represent a nitrogen atom.

$R^1$ and $R^2$ independently represent a hydrogen atom, an alkyl group having 1 to 6 carbon atoms or an alkoxy group having 1 to 6 carbon atoms. $R^1$ and $R^2$ are preferably a hydrogen atom or a methyl group, and more preferably a hydrogen atom.

$R^3$ and $R^4$ independently represent an alkyl group having 1 to 6 carbon atoms or an alkoxy group having 1 to 6 carbon atoms. $R^3$ and $R^4$ are preferably a methyl group.

m represents an integer in the range of 0 to 4, provided that, in the case when m is at least 2, each $R^3$ may be the same or different. n represents an integer in the range of 0 to 5, provided that, in the case when n is at least 2, each $R^4$ may be the same or different. Preferably both of m and n represent 0.

An alkyl group having 1 to 6 carbon atoms for $R^1$ through $R^4$ in the formula (1) includes, for example, methyl, ethyl, propyl, isopropyl, butyl, isobutyl, 1-methylpropyl, t-butyl, pentan-1-yl, 3-methylbutyl, 2,2-dimethylpropyl and hexan-1-yl groups. An alkoxy group having 1 to 6 carbon atoms for $R^1$ through $R^4$ in the formula (1) includes, for example, methoxy, ethoxy, propoxy, butoxy, pentanoxy and hexanoxy groups.

The compound (1) preferably has the same pyridyl-substituted phenylene groups or the same phenyl-substituted pyridylene groups at all of 1, 2, 4, and 5 positions of a benzene ring because of ease in synthesis.

Hydrogen atoms in the formula (1) each can independently be replaced with a deuterium atom.

As specific examples of the compound (1), the following compounds (A1) through (A25) can be mentioned, but, the compound (1) of the present invention is not limited thereto.

(A1)

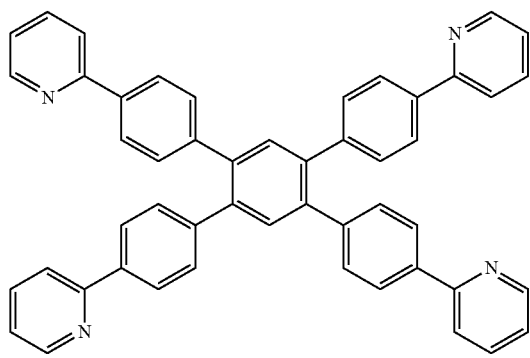

(A2)

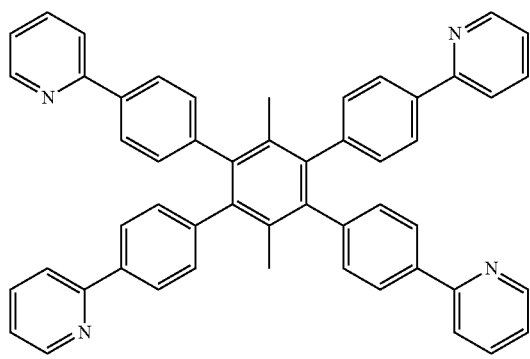

(A3)

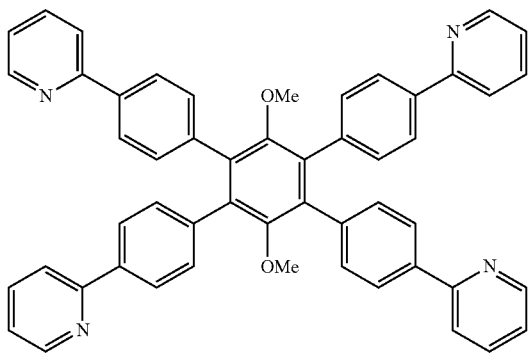

(A4)

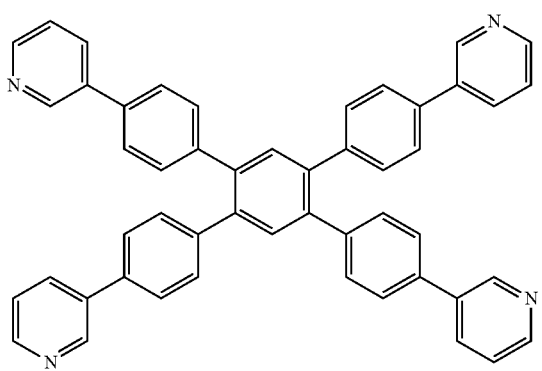

(A5)

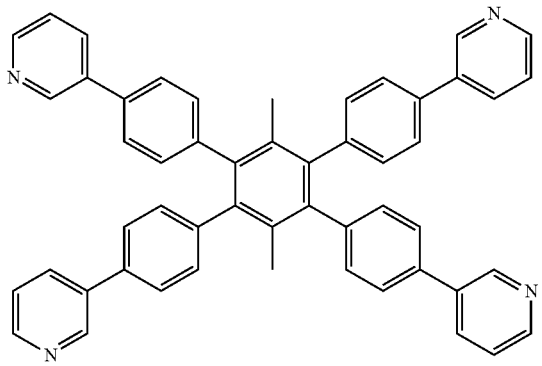

(A6)

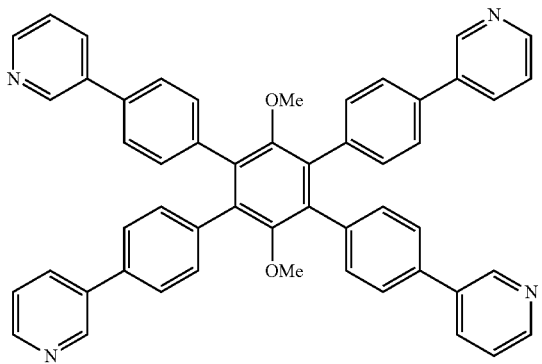

(A7)
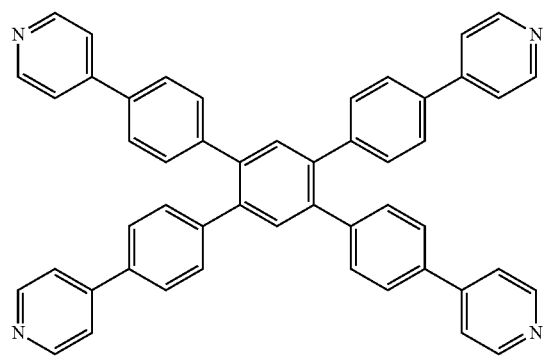
(A8)
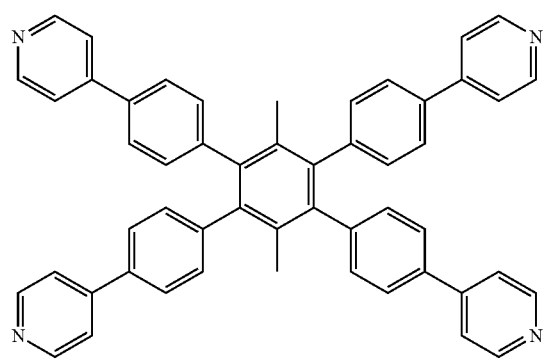
(A9)
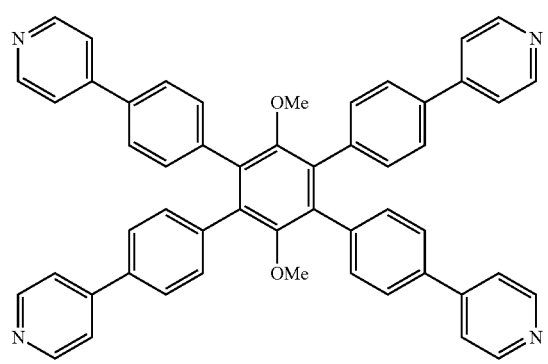
(A10)
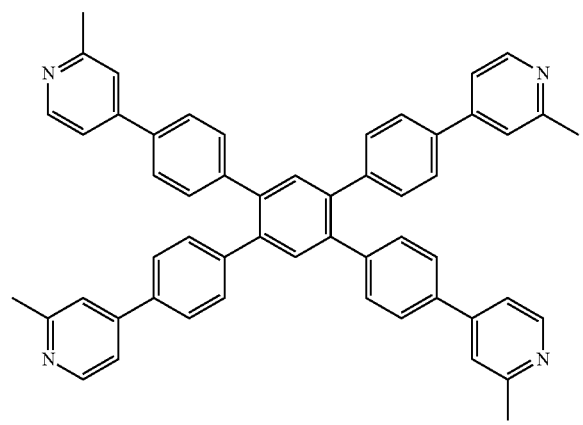
(A11)
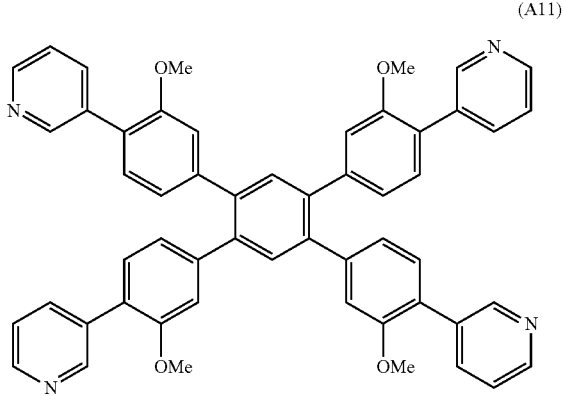
(A12)
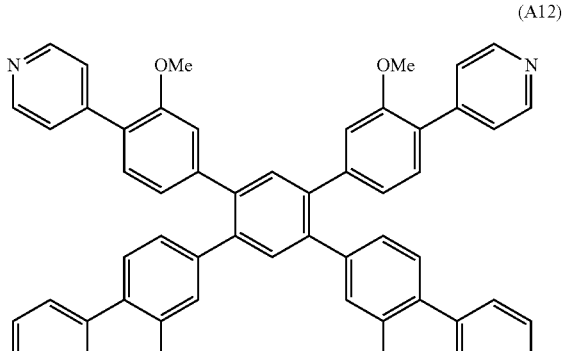
(A13)
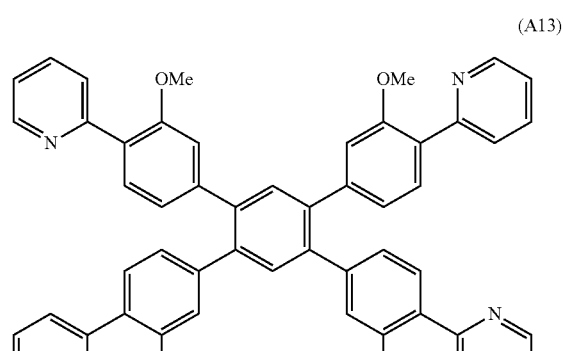
(A14)
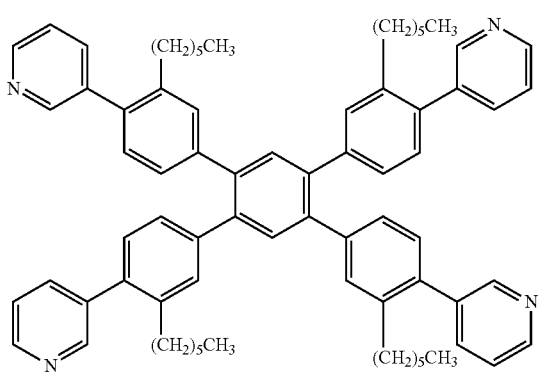

(A15)
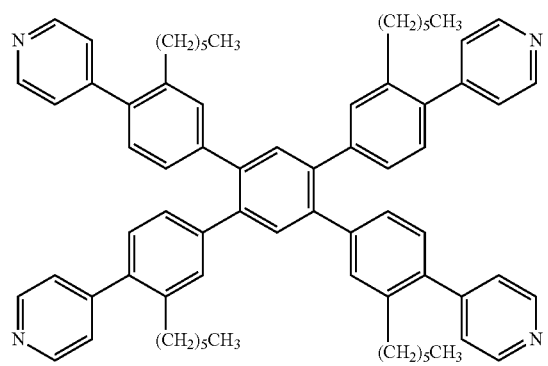
(A19)
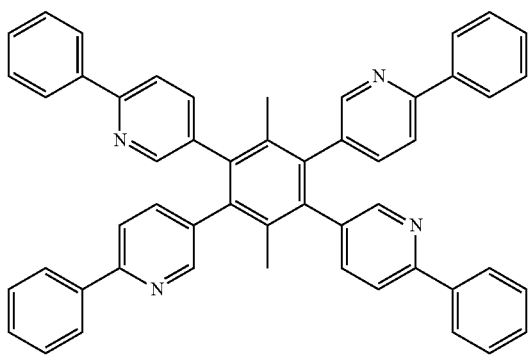
(A16)
(A20)
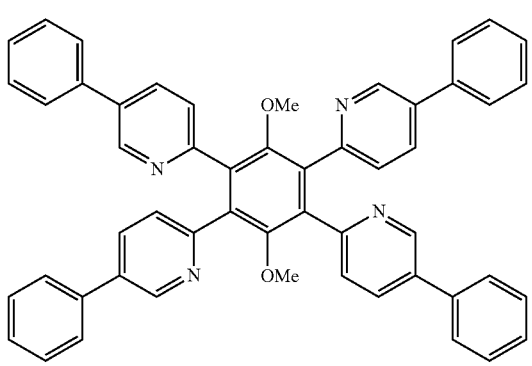
(A17)
(A21)
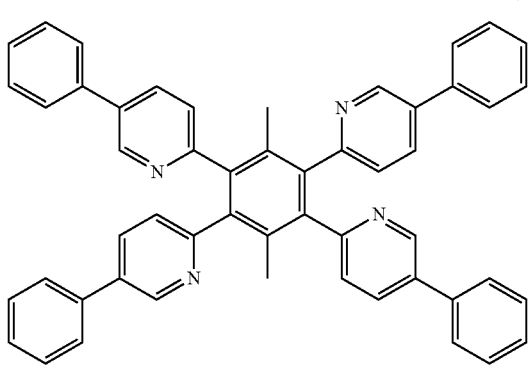
(A18)
(A22)
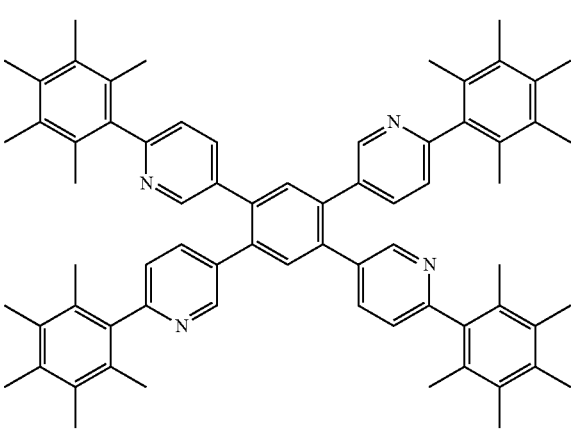

-continued (A23)

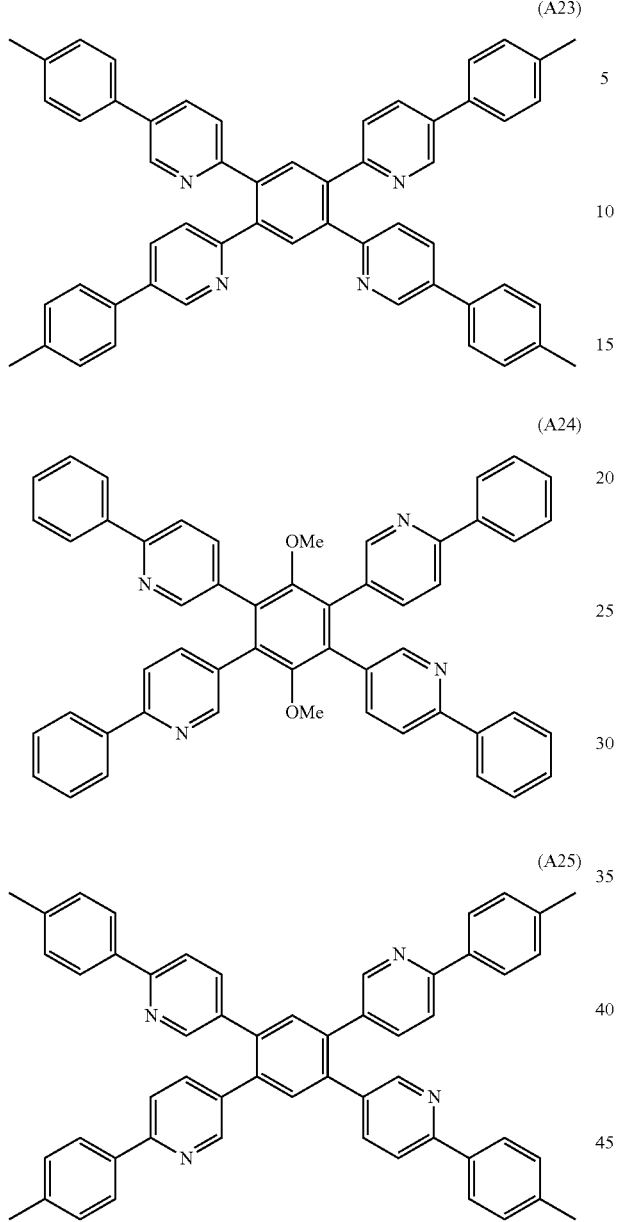

(A24)

(A25)

The process for preparing the compound (1) will be described.

The compound (1) is prepared by a process comprising a step represented by the following reaction scheme (hereinafter referred to as "step 1" when appropriate).

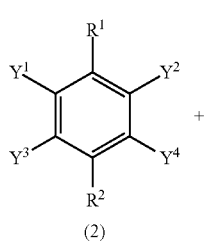

-continued

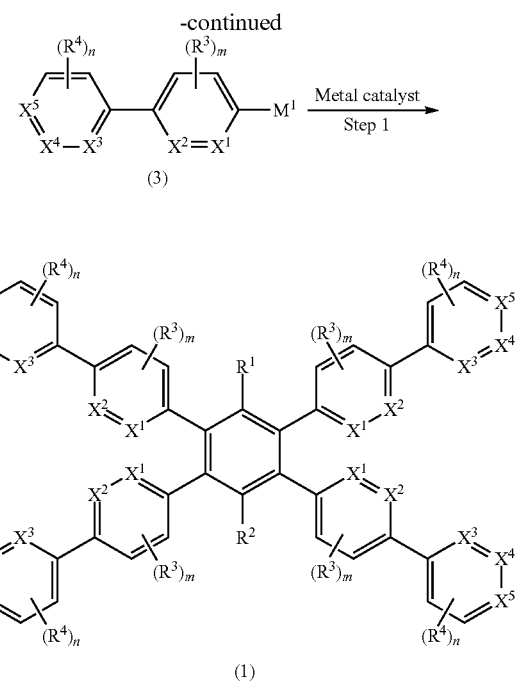

In the formulas (1), (2) and (3), one of $X^1$ through $X^5$ represents a nitrogen atom and the remainders of $X^1$ through $X^5$ represent a carbon atom. $R^1$ and $R^2$ independently represent a hydrogen atom, an alkyl group having 1 to 6 carbon atoms or an alkoxy group having 1 to 6 carbon atoms. $R^3$ and $R^4$ independently represent an alkyl group having 1 to 6 carbon atoms or an alkoxy group having 1 to 6 carbon atoms. m represents an integer in the range of 0 to 4, provided that, in the case when m is at least 2, each $R^3$ may be the same or different. n represents an integer in the range of 0 to 5, provided that, in the case when n is at least 2, each $R^4$ may be the same or different. $Y^1$ through $Y^4$ independently represent a leaving group. $M^1$ represents a metallic group or a heteroatom group.

The process comprising the step 1 will be specifically described below, but by no means limits the scope of the invention.

The compound represented by the formula (3) (hereinafter referred to as "compound (3)" when appropriate) can be prepared, for example, by a process described in JP 2008-280330 A, paragraphs [0061] through [0076]. $M^1$ in the formula (3) includes, for example, $ZnR^5$, $MgR^6$, $Sn(R^7)_3$ and $B(OR^8)_2$, where $R^5$ and $R^6$ independently represent a chlorine, bromine or iodine atom, $R^7$ represents an alkyl group having 1 to 4 carbon atoms or a phenyl group, $R^8$ represents a hydrogen atom, an alkyl group having 1 to 4 carbon atoms or a phenyl group, provided that two $R^8$s in the $B(OR^8)_2$ may be the same or different, and two $R^8$s in the $B(OR^8)_2$ may be bonded together with the oxygen atoms and the boron atom to form a ring.

As specific examples of the $B(OR^8)_2$ in the compound (3), there can be mentioned $B(OH)_2$, $B(OMe)_2$, $B(O^iPr)_2$, $B(OBu)_2$ and $B(OPh)_2$. The two $R^8$s in $B(OR^8)_2$ may form a ring together with the oxygen atoms and the boron atom, thus, $B(OR^8)_2$ may form the following groups (I) through (VI), for example. Of these groups, group (II) is preferable in view of high reaction yield.

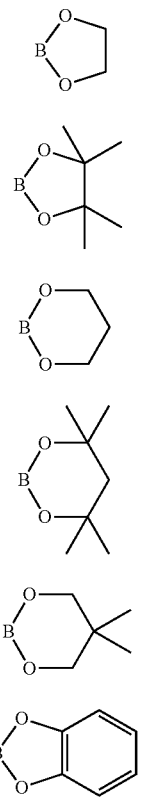

(I)

(II)

(III)

(IV)

(V)

(VI)

The leaving groups represented by $Y^1$ through $Y^4$ in the compound of the formula (2) (which compound is hereinafter referred to as "compound (2)" when appropriate) include, for example, a chlorine atom, a bromine atom, an iodine atom, a trifluoromethylsulfonyloxy (OTf) group, a methanesulfonyloxy (OMs) group, a chloromethanesulfonyloxy group and a p-toluenesulfonyloxy (OTs) group.

As specific examples of the compound (2), the following compounds (B1) through (B25) can be mentioned, but, the compound (2) used in the present invention is not limited thereto. In these compounds, $R^1$ and $R^2$ independently represent a hydrogen atom, an alkyl group having 1 to 6 carbon atoms or an alkoxy group having 1 to 6 carbon atoms.

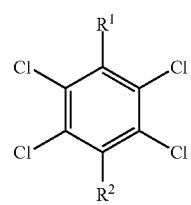

(B1)

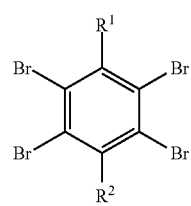

(B2)

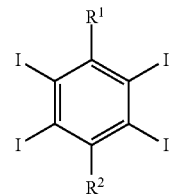

(B3)

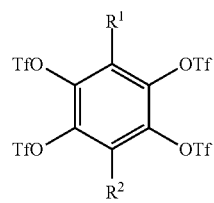

(B4)

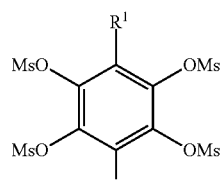

(B5)

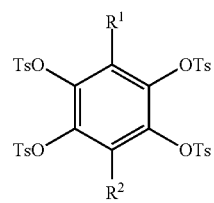

(B6)

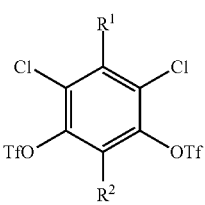

(B7)

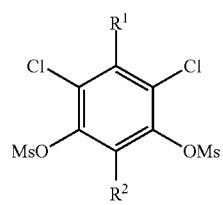

(B8)

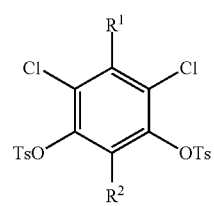

(B9)

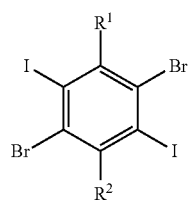 (B10)
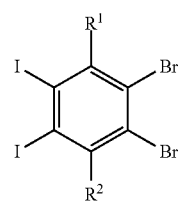 (B11)
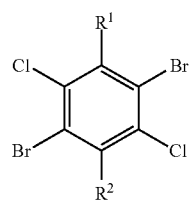 (B12)
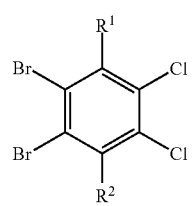 (B13)
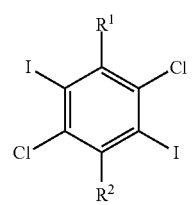 (B14)
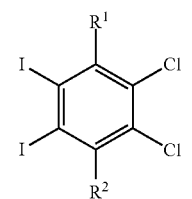 (B15)
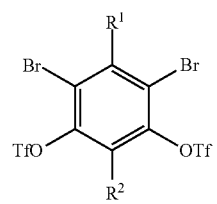 (B16)
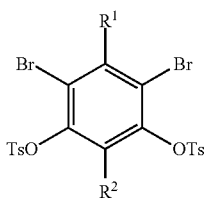 (B17)
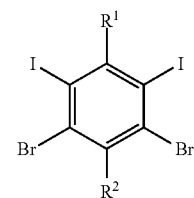 (B18)
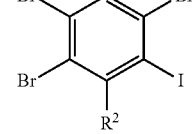 (B19)
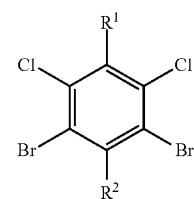 (B20)
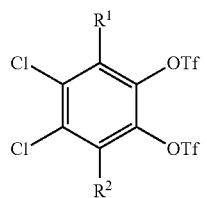 (B21)
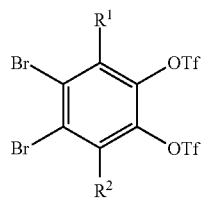 (B22)
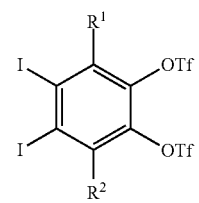 (B23)

-continued

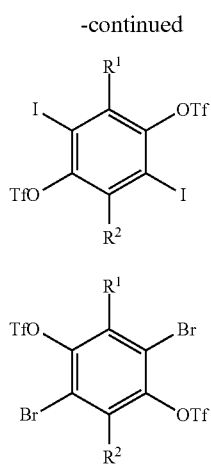

(B24)

(B25)

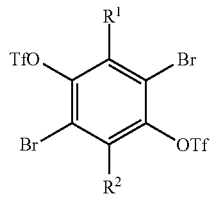

In the step 1, the compound (3) is reacted with the compound (2) in the presence of a metal catalyst and, if required, further in the presence of a base to give the 1,2,4,5-substituted phenyl compound (1) of the present invention. This reaction can be conducted by adopting the conventional coupling reaction conditions in, for example, Suzuki-Miyaura reaction, Negishi reaction, Tamao-Kumada reaction and Stille reaction. The target compound can be obtained with a high yield by adopting such reaction conditions.

In the step 1, a palladium catalyst and a nickel catalyst are preferably used as the metal catalyst.

As specific example of the palladium catalyst, there can be mentioned palladium salts such as palladium chloride, palladium acetate, palladium trifluoroacetate and palladium nitrate; and complex compounds such as n-allylpalladium chloride dimmer, palladium acetylacetonate, tris(dibenzylideneacetone)dipalladium, dichlorobis(triphenylphosphine)palladium, tetrakis(triphenylphosphine)palladium and dichloro[1,1'-bis(diphenylphosphino)ferrocene]palladium.

Of these, palladium complex compounds having a tertiary phosphine as a ligand are preferable because of high reaction yield.

Palladium complex compounds having a tertiary phosphine as a ligand can also be synthesized in a reaction system containing a palladium salt or a palladium complex compound and a tertiary phosphine added therein.

As specific examples of the tertiary phosphine used, there can be mentioned triphenylphosphine, trimethylphosphine, tributylphosphine, tri(tert-butyl)phosphine, tricyclohexylphosphine, tert-butyldiphenylphosphine, 9,9-dimethyl-4,5-bis(diphenylphosphino)xanthene, 2-(diphenylphosphino)-2'-(N,N-dimethylamino)biphenyl, 2-(di-tert-butylphosphino)biphenyl, 2-(dicyclohexylphosphino)biphenyl, bis(diphenylphosphino)methane, 1,2-bis(diphenylphosphino)ethane, 1,3-bis(diphenylphosphino)propane, 1,4-bis(diphenylphosphino)butane, 1,1'-bis(diphenylphosphino)ferrocene, tri-(2-furyl)phosphine, tri-(o-tolyl)phosphine, tris(2,5-xylyl)phosphine, (±)-2,2'-bis(diphenylphosphino)-1,1'-binaphthyl, 2-dicyclohexylphosphino-2',4',6'-triisopropylbiphenyl and 2-dicyclohexylphosphino-2',6'-dimethoxybiphenyl.

Of these, 2-dicyclohexylphosphino-2',4',6'-triisopropylbiphenyl is preferable in view of ease in availability and high reaction yield.

The molar ratio of the tertiary phosphine to the palladium salt or the palladium complex compound is preferably in the range of 1:10 to 10:1, and more preferably 1:2 to 5:1 because of high reaction yield.

As specific example of the nickel catalyst, there can be mentioned [1,1'-bis(diphenylphosphino)ferrocene]nickel(II) dichloride, [1,2-bis(diphenylphosphino)ethane]nickel(II) dichloride, [1,3-bis(diphenylphosphino)propane]nickel(II) dichloride, [1,1'-bis(diphenylphosphino)propane]nickel(II) dichloride, [1,2-bis(diphenylphosphino)ethane]nickel(II) dichloride and [1,3-bis(diphenylphosphino)propane]nickel (II) dichloride.

The base capable of being used in the step 1 includes, for example, sodium hydroxide, potassium hydroxide, sodium carbonate, potassium carbonate, lithium carbonate, cesium carbonate, tripotassium phosphate, sodium phosphate, sodium fluoride, potassium fluoride and cesium fluoride. Of these, tripotassium phosphate is preferable because of high reaction yield.

The molar ratio of the base to the compound (3) is preferably in the range of 1:2 to 10:1, and more preferably 1:1 to 3:1 because of high reaction yield.

The molar ratio of the compound (2) to the compound (3) which are used in the step 1 is preferably in the range of 1:4 to 1:10, and more preferably 1:4 to 1:8 because of high reaction yield.

A reaction medium capable of being used in the step 1 includes, for example, water, dimethylsulfoxide, dimethylformamide, tetrahydrofuran, dioxane, toluene, benzene, diethyl ether, ethanol, methanol and xylene. These reaction mediums may be used either alone or in combination. Of these, a mixed medium of toluene and ethanol is preferable because of high reaction yield.

The reaction in the step 1 can be conducted at a temperature appropriately chosen in a range of 0° C. to 150° C. A temperature of 60° C. to 100° C. is especially preferable because of high reaction yield.

The compound (1) according to the present invention can be obtained by conducting the conventional treating procedure after completion of the step 1. If desired, the prepared compound is purified by, for example, recrystallization, column chromatography or sublimation.

The 1,2,4,5-substituted phenyl compound according to the present invention can also be prepared by a process comprising a step represented by the following reaction scheme.

The compound (1) can also be prepared by a process comprising a step represented by the following reaction scheme (which step is hereinafter referred to as "step 2" when appropriate).

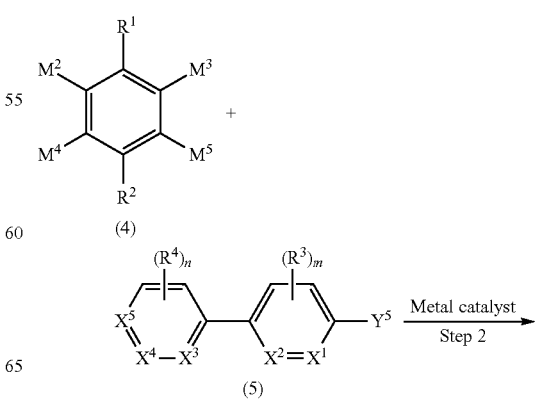

-continued

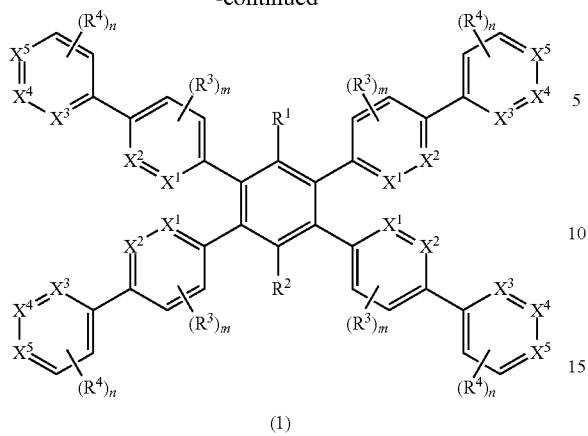

(1)

In the formulas (1), (4) and (5), one of $X^1$ through $X^5$ represents a nitrogen atom and the remainders of $X^1$ through $X^5$ represent a carbon atom. $R^1$ and $R^2$ independently represent a hydrogen atom, an alkyl group having 1 to 6 carbon atoms or an alkoxy group having 1 to 6 carbon atoms. $R^3$ and $R^4$ independently represent an alkyl group having 1 to 6 carbon atoms or an alkoxy group having 1 to 6 carbon atoms. m represents an integer in the range of 0 to 4, provided that, in the case when m is at least 2, each $R^3$ may be the same or different. n represents an integer in the range of 0 to 5, provided that, in the case when n is at least 2, each $R^4$ may be the same or different. $M^2$ through $M^5$ independently represent a metallic group or a heteroatom group. $Y^5$ represents a leaving group.

The metallic group or the hetero group for $M^2$ through $M^5$ in the compound represented by the formula (4) (which compound is hereinafter referred to as "compound (4)" when appropriate) includes, for example, $Sn(R^7)_3$ and $B(OR^8)_2$, where $R^7$ represents an alkyl group having 1 to 4 carbon atoms or a phenyl group, and $R^8$ represents a hydrogen atom, an alkyl group having 1 to 4 carbon atoms or a phenyl group, provided that two $R^8$s in the $B(OR^8)_2$ may be the same or different, and two $R^8$s in the $B(OR^8)_2$ may be bonded together with the oxygen atoms and the boron atom to form a ring.

As specific examples of the $B(OR^8)_2$ in the compound (4), there can be mentioned $B(OH)_2$, $B(OMe)_2$, $B(O^iPr)_2$, $B(OBu)_2$ and $B(OPh)_2$. The two $R^8$s in $B(OR^8)_2$ may form a ring together with the oxygen atoms and the boron atom, thus, $B(OR^8)_2$ may form the following groups (I) through (VI), for example. Of these groups, group (II) is preferable in view of high reaction yield.

(I)

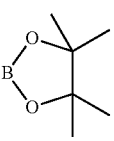

(II)

(III)

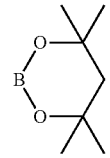

(IV)

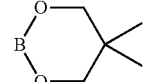

(V)

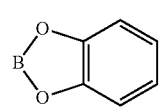

(VI)

The compound represented by the formula (5) (which compound is hereinafter referred to as "compound (5)" when appropriate) can be prepared, for example, by a process described in Synlett, vol. 6, 852-854, 2003.

The leaving group represented by $Y^5$ in the compound (5) includes, for example, a chlorine atom, a bromine atom, an iodine atom, a trifluoromethylsulfonyloxy group, a methanesulfonyloxy group, a chloromethanesulfonyloxy group and a p-toluenesulfonyloxy group.

The step 2 can be conducted under reaction conditions and by procedures, which are similar to those adopted in the step 1. The compound (1) according to the present invention can be obtained by conducting the conventional treating procedure after completion of the step 2. If desired, the prepared compound is purified by, for example, recrystallization, column chromatography or sublimation.

The organic electroluminescent device according to the present invention comprises the above-mentioned 1,2,4,5-substituted phenyl compound [compound (1)] as a constituent. More specifically the organic EL device has a multilayer structure comprising a thin-film layer or layers comprised of the compound (1). The constitution of the multilayer structure comprising the organic EL thin-film layer or layers is not particularly limited, and may be the same as those which are conventionally adopted for fluorescent or phosphorescent organic EL devices.

A typical example of an organic EL device having a thin film layer comprised of the compound (1) of the present invention is illustrated in FIG. 1. This organic EL device comprises a glass substrate 1 with transparent ITO electrode, and organic compound layers comprising hole injection layer 2, a hole transport layer 3, a light emitting layer 4 and an electron transport layer 5 comprised of the compound (1) of the present invention, which are formed in this order on the glass substrate 1, and further a cathode layer 6.

The process for producing the organic EL device comprising the 1,2,4,5-substituted phenyl compound [compound (1)] according to the present invention is not particularly limited. Thin films for the multilayer structure can be formed by, for example, vacuum deposition. The vacuum deposition can be conducted using a conventional vacuum deposition apparatus. However, in consideration of the tact time and cost for the production of the organic EL device, the degree of vacuum at the vacuum deposition is chosen preferably in the range of approximately $1 \times 10^{-2}$ Pa to $1 \times 10^{-5}$ Pa, which can be achieved, for example, by the conventionally used diffusion pump, turbo-molecular pump or cryopump. The rate of vacuum deposition varies depending upon the thickness of thin film, but the deposition rate is preferably in the range of 0.005 nm/sec to 1.0 nm/sec.

The thin films can also be formed by, spin coating, ink jetting, casting or dipping using the conventional apparatus.

EXAMPLES

The invention will now be described more specifically by the following examples and comparative examples, but the scope of the invention is by no means limited thereto.

Example 1

Synthesis of Compound (1)

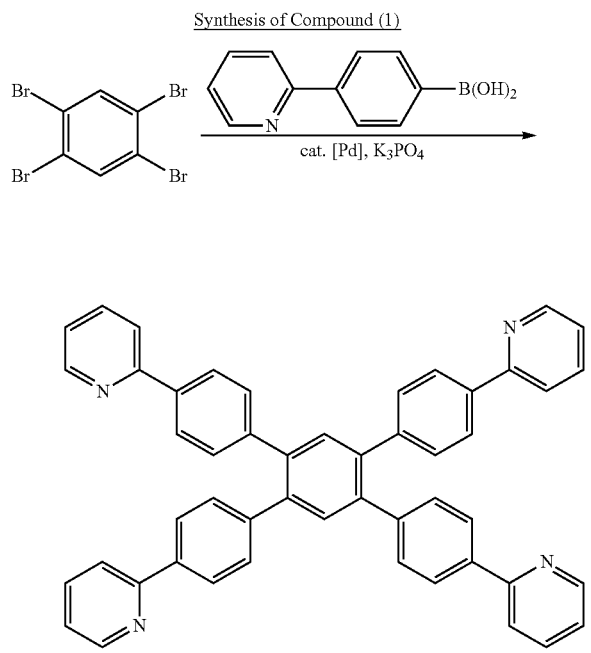

In a stream of argon, 1.00 g (2.5 mmol) of 1,2,4,5-tetrabromobenzene, 4.04 g (20 mmol) of 4-(2-pyridyl)phenylboric acid, 28.5 mg (0.13 mmol) of palladium acetate, 121 mg (0.25 mmol) of 2-dicyclohexylphosphino-2',4',6'-triisopropylbiphenyl, and 5.39 g (25 mmol) of tripotassium phosphate were dissolved in a mixed solvent comprised of 10 mL of toluene and 1 mL of water. The obtained solution was heated under reflux for 44 hours. The reaction mixture was cooled to room temperature, and then, diluted with methanol and the solid was filtered. The thus-obtained crude product was purified by silica gel chromatography using a mixed solvent comprised of chloroform and hexane (2:1~1:0) as a developing solvent to give 1.38 g of the target 4,4''-di(2-pyridyl)-4',5'-bis[4-(2-pyridyl)phenyl]-1,1':2',1''-terphenyl as a white solid (yield: 79%).

$^1$H-NMR(CDCl$_3$): δ7.21-7.53 (m, 4H), 7.44 (d, J=8.44 Hz, 8H), 7.69 (s, 2H), 7.53-7.79 (m, 8H), 7.94 (d, J=8.48 Hz, 8H), 8.70 (d, J=4.56 Hz, 4H)

Example 2

Synthesis of Compound (1)

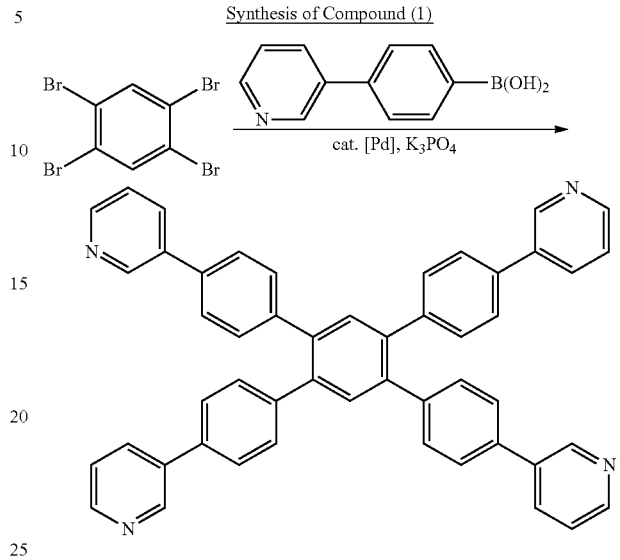

In a stream of argon, 1.00 g (2.5 mmol) of 1,2,4,5-tetrabromobenzene, 4.04 g (20 mmol) of 4-(3-pyridyl)phenylboric acid, 28.5 mg (0.13 mmol) of palladium acetate, 121 mg (0.25 mmol) of 2-dicyclohexylphosphino-2',4',6'-triisopropylbiphenyl, and 5.39 g (25 mmol) of tripotassium phosphate were dissolved in a mixed solvent comprised of 20 mL of dioxane and 6 mL of water. The obtained solution was heated under reflux for 21 hours. The reaction mixture was cooled to room temperature, and then, diluted with water and the solid was filtered. The thus-obtained crude product was purified by silica gel chromatography using chloroform as a developing solvent to give 1.35 g of the target 4,4''-di(3-pyridyl)-4',5'-bis[4-(3-pyridyl)phenyl]-1,1':2',1''-terphenyl as a white solid (yield: 77%).

$^1$H-NMR(CDCl$_3$): δ7.46 (d, J=8.28 Hz, 8H), 7.48-7.56 (m, 4H), 7.57 (d, J=8.32 Hz, 8H), 7.69 (s, 2H), 8.07 (d, J=7.12 Hz, 4H), 8.63 (dd, J=1.48, 4.96 Hz, 4H), 8.92 (d, J=1.96 Hz, 4H)

Example 3

Synthesis of Compound (1)

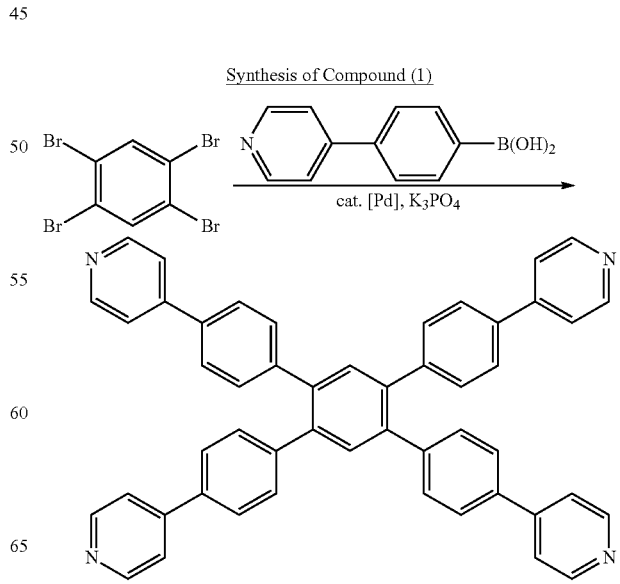

In a stream of argon, 65.9 mg (0.17 mmol) of 1,2,4,5-tetrabromobenzene, 200 mg (1.01 mmol) of 4-(4-pyridyl)phenylboric acid, 1.88 mg (0.0084 mmol) of palladium acetate, 8.60 mg (0.021 mmol) of 2-dicyclohexylphosphino-2',6'-dimethoxybiphenyl, and 640 mg (3.02 mmol) of tripotassium phosphate were dissolved in 100 mL of toluene. The obtained solution was heated under reflux for 48 hours. The reaction mixture was cooled to room temperature, and then, diluted with 300 mL of chloroform, and the solid was filtered. The obtained organic phase was concentrated, and the thus-obtained crude product was purified by silica gel chromatography using a mixed solvent comprised of chloroform and methanol (99:120:1) as a developing solvent to give 20 mg of the target 4,4''-di(4-pyridyl)-4',5'-bis[4-(4-pyridyl)-phenyl]-1,1':2',1''-terphenyl as a white solid (yield: 17%).

$^1$H-NMR(CDCl$_3$): δ7.52 (s, 2H), 7.54 (d, J=6.21 Hz, 8H), 7.65 (d, J=8.28 Hz, 8H), 7.85 (d, J=8.28 Hz, 8H), 8.68 (d, J=6.21 Hz, 8H)

Example 4

Synthesis of Compound (1)

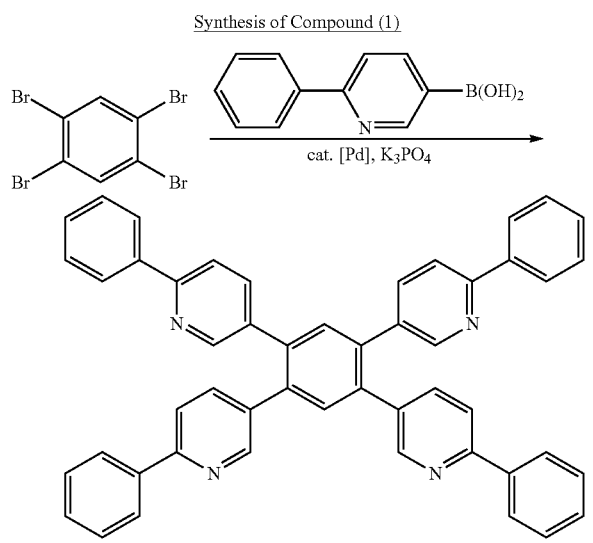

In a stream of argon, 0.787 g (2.0 mmol) of 1,2,4,5-tetrabromobenzene, 3.19 g (16 mmol) of 2-phenylpyridin-5-ylboric acid, 22.5 mg (0.10 mmol) of palladium acetate, 95.3 mg (0.20 mmol) of 2-dicyclohexylphosphino-2',4',6'-triisopropylbiphenyl, and 4.25 g (20 mmol) of tripotassium phosphate were dissolved in a mixed solvent comprised of 25 mL of toluene and 5.0 mL of water. The obtained solution was heated under reflux for 72 hours. The reaction mixture was cooled to room temperature, and then, subjected to extraction with chloroform. The extract was distilled under a reduced pressure to remove all volatile materials. Then the residue was diluted with methanol and the solid was filtered. The thus-obtained crude product was recrystallized from o-xylene to give 0.743 g of the target 1,2,4,5-tetrakis(2-phenylpyridin-5-yl)benzene as a white solid (yield: 54%).

$^1$H-NMR(CDCl$_3$): δ7.41-7.52 (m, 12H), 7.67 (d, J=8.2 Hz, 4H), 7.72 (s, 2H), 7.72 (d, J=8.2 Hz, 4H), 8.02 (d, J=7.0 Hz, 8H), 8.70 (s, 4H)

Example 5

Synthesis of Compound (1)

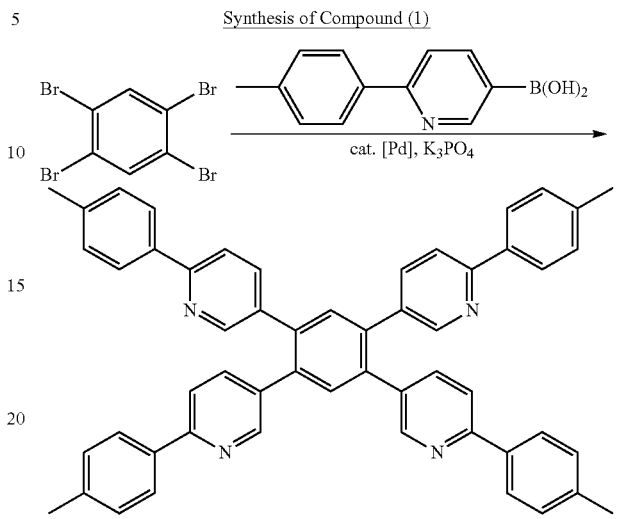

In a stream of argon, 0.50 g (1.3 mmol) of 1,2,4,5-tetrabromobenzene, 2.16 g (10.2 mmol) of 2-(4-methylphenyl)pyridin-5-ylboric acid, 14.3 mg (0.06 mmol) of palladium acetate, 60.5 mg (0.13 mmol) of 2-dicyclohexylphosphino-2',4',6'-triisopropylbiphenyl, and 2.70 g (13 mmol) of tripotassium phosphate were dissolved in a mixed solvent comprised of 20 mL of toluene and 2 mL of water. The obtained solution was heated under reflux for 72 hours. The reaction mixture was diluted with water, and then, subjected to extraction with chloroform. The extract was distilled under a reduced pressure to remove the solvent. The solid was recrystallized from 25 mL of o-xylene to give 901 mg of the target 1,2,4,5-tetrakis[2-(4-methylphenyl)pyridin-5-yl)benzene as a white solid (yield: 95%).

$^1$H-NMR(CDCl$_3$): δ2.44 (s, 12H), 7.30 (d, J=8.28 Hz, 8H), 7.63 (d, J=8.24 Hz, 4H), 7.68 (d, J=8.40 Hz, 4H), 7.69 (s, 2H), 7.91 (d, J=8.20 Hz, 8H), 8.67 (s, 4H)

Example 6

Production of Organic EL Device using Compound (1) Synthesized in Example 1, and Evaluation Thereof A 2 mm width glass substrate with a transparent indium-tin oxide (ITO) electrode was prepared, which had a stripe pattern comprised of ITO film. The substrate was washed with isopropyl alcohol and then surface-treated by irradiation with ozone-ultraviolet rays. Using the surface-treated glass substrate, an organic EL device with an emission area of 4 mm$^2$ having a multilayer structure as illustrated in FIG. 1 was manufactured by forming respective layers by vacuum deposition.

The surface-treated glass substrate was placed in a vacuum deposition chamber, and the inner pressure was reduced to $1.0 \times 10^{-4}$ Pa.

As illustrated in FIG. 1, organic compound layers, i.e., a hole injection layer 2, a hole transport layer 3, an emitting layer 4 and an electron transport layer 5 were formed in this order on the above-mentioned glass substrate 1. Further, a cathode layer 6 was formed.

The hole injection layer 2 was formed by vacuum-depositing phtalocyanine copper(II), previously purified by sublimation, into a thickness of 25 nm. The hole transport layer 3 was formed by vacuum-depositing N,N'-di(1-naphthyl)-N,N'-diphenylbenzidine (NPD) into a thickness of 45 nm.

The emitting layer 4 was formed by vacuum-depositing a mixture of 97 mass % of 2-t-butyl-9,10-di(2-naphthyl)-anthracene (TBADN) and 3 mass % of 4,4'-bis[4-(di-p-tolylamino)phenylethen-1-yl]biphenyl (DPAVBi) into a thickness of 40 nm.

The electron transport layer 5 was formed by vacuum-depositing 4,4"-di(2-pyridyl)-4',5'-bis[4-(2-pyridyl)-phenyl]-1,1':2',1"-terphenyl, synthesized in Example 1, into a thickness of 20 nm.

The vacuum deposition of each organic material was conducted by subjecting each organic material to electric resistance heating to form a thin film at a deposition rate of 0.3 nm/sec to 0.5 nm/sec.

Then, a metal mask was arranged so as to be orthogonal to the ITO stripe, and a cathode layer 6 was vacuum-deposited. The vacuum deposition of the cathode layer 6 was conducted so as to have a double layer structure comprising a lithium fluoride layer with a thickness of 1.0 nm and an aluminum layer with a thickness of 100 nm.

The measurement of thickness of each organic material thin film layer was conducted by stylus profilometer (DEKTAK).

Finally the thus-obtained assembly of multi-layers was encapsulated with a glass cap and ultraviolet ray-curable epoxy resin (available from Nagase Chemtex Corporation). The encapsulation was conducted in a nitrogen atmosphere having an oxygen-and-moisture content of below 1 ppm within a glove box.

Luminous properties of the thus-manufactured organic EL device were evaluated by applying a direct current and using a luminance meter "BM-9" available from Topcon Corporation. The luminous properties, i.e., voltage (V), luminance ($cd/m^2$), current efficiency (cd/A) and power efficiency (lm/W) were measured at a current density of 20 $mA/cm^2$. The luminance half-life was measured as the luminance reaches a half-value of the initial luminance when the device is continuously illuminated.

The luminous properties of the manufactured organic EL device were as follows. Voltage 3.8 V, luminance 2,070 $cd/m^2$, current efficiency 10.4 cd/A, power efficiency 8.5 lm/W. Luminance half-life of the device was 1,550 hours.

Example 7

Production of Organic EL Device using Compound (1) Synthesized in Example 4, and Evaluation Thereof By the same procedures as described in Example 6, an organic EL device was manufactured except that the electron transport layer 5 having a thickness of 20 nm was formed from 1,2,4,5-tetrakis(2-phenylpyridin-5-yl)benzene, synthesized in Example 4, instead of the compound (1) synthesized in Example 1, with all other procedures remaining the same.

The thus-manufactured EL device exhibited a voltage of 5.3 V, a luminance of 1,691 $cd/m^2$, a current efficiency of 8.5 cd/A, and a power efficiency of 5.1 lm/W.

Example 8

Production of Organic EL Device using Compound (1) Synthesized in Example 5, and Evaluation Thereof By the same procedures as described in Example 6, an organic EL device was manufactured except that the electron transport layer 5 having a thickness of 20 nm was formed from 1,2,4,5-tetrakis[2-(4-methylphenyl)pyridin-5-yl]benzene, synthesized in Example 5, instead of the compound (1) synthesized in Example 1, with all other procedures remaining the same.

The thus-manufactured EL device exhibited a voltage of 6.3 V, a luminance of 1629 $cd/m^2$, a current efficiency of 8.5 cd/A, and a power efficiency of 4.2 lm/W.

Comparative Example 1

Production of Organic EL Device using Conventional Organic EL Material, and Evaluation Thereof By the same procedures as described in Example 6, an organic EL device was manufactured except that the electron transport layer 5 having a thickness of 20 nm was formed from a conventional organic EL material, tris(8-quinolinolato)-aluminum(III) (Alq), instead of the compound (1) synthesized in Example 1, with all other procedures remaining the same.

The thus-manufactured EL device exhibited a voltage of 6.4 V, a luminance of 1,664 $cd/m^2$, a current efficiency of 8.3 cd/A, and a power efficiency of 4.1 lm/W. Luminance half-life of the device was 1,500 hours.

INDUSTRIAL APPLICABILITY

A fluorescent or phosphorescent organic electroluminescent device comprising as a constituent the compound (1) according to the present invention exhibits a low power consumption and an enhanced life as compared with organic electroluminescent devices made of known materials. The compound (1) of the present invention can be widely applied to an electron transport layer of organic electroluminescent devices and to the other layers including an luminescent host layer using a luminescent material. The compound (1) can be applied to organic electroluminescent devices having various structures comprising fluorescent materials or phosphorescent materials. The organic electroluminescent device of the present invention can be used broadly to fields including flat panel displays, and lighting equipments to which low power consumption and long life are required.

The invention claimed is:

1. A 1,2,4,5-substituted phenyl compound represented by the following formula (1):

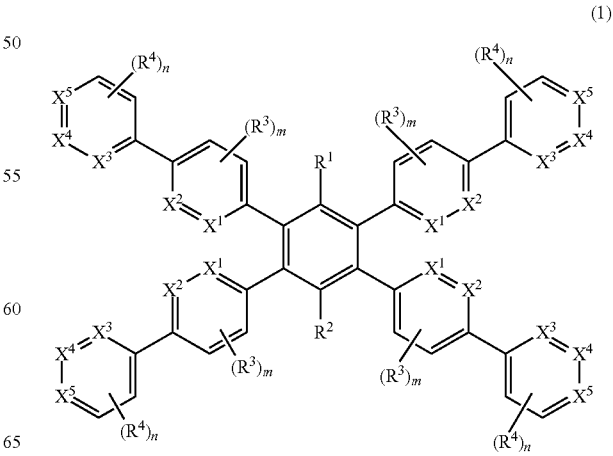

(1)

wherein one of $X^3$ and $X^4$ represents a nitrogen atom and the other of $X^3$ and $X^4$ represents a carbon atom, and $X^1$, $X^2$ and $X^5$ represent a carbon atom;

$R^1$ and $R^2$ independently represent a hydrogen atom, an alkyl group having 1 to 6 carbon atoms or an alkoxy group having 1 to 6 carbon atoms;

$R^3$ and $R^4$ independently represent an alkyl group having 1 to 6 carbon atoms or an alkoxy group having 1 to 6 carbon atoms; and m represents an integer in the range of 0 to 4, provided that, in the case when m is at least 2, each $R^3$ may be the same or different; and n represents an integer in the range of 0 to 4, provided that, in the case when n is at least 2, each $R^4$ may be the same or different.

2. A process for preparing the 1,2,4,5-substituted phenyl compound of claim 1, comprising subjecting a compound represented by the following formula (2) to a coupling reaction with a compound represented by the following formula (3) in the presence of a metal catalyst and if required, further in the presence of a base;

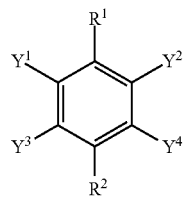

(2)

wherein $Y^1$ through $Y^4$ independently represent a leaving group, $R^1$ and $R^2$ independently represent a hydrogen atom, an alkyl group having 1 to 6 carbon atoms or an alkoxy group having 1 to 6 carbon atoms;

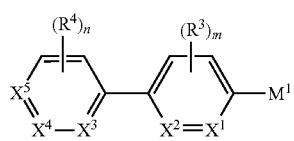

(3)

wherein one of $X^1$ through $X^5$ represents a nitrogen atom and the remainders of $X^1$ through $X^5$ represent a carbon atom; $R^3$ and $R^4$ independently represent an alkyl group having 1 to 6 carbon atoms or an alkoxy group having 1 to 6 carbon atoms; and m represents an integer in the range of 0 to 4, provided that, in the case when m is at least 2, each $R^3$ may be the same or different; and n represents an integer in the range of 0 to 5, provided that, in the case when n is at least 2, each $R^4$ may be the same or different; and $M^1$ represents a metallic group or a heteroatom group.

3. A process for preparing the 1,2,4,5-substituted phenyl compound of claim 1, comprising subjecting a compound represented by the following formula (4) to a coupling reaction with a compound represented by the following formula (5) in the presence of a metal catalyst and if required, further in the presence of a base:

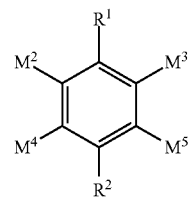

(4)

wherein $R^1$ and $R^2$ independently represent a hydrogen atom, an alkyl group having 1 to 6 carbon atoms or an alkoxy group having 1 to 6 carbon atoms, and $M^2$ through $M^5$ independently represent a metallic group or a heteroatom group;

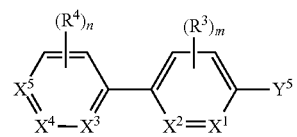

(5)

wherein one of $X^1$ through $X^5$ represents a nitrogen atom and the remainders of $X^1$ through $X^5$ represent a carbon atom; $R^3$ and $R^4$ independently represent an alkyl group having 1 to 6 carbon atoms or an alkoxy group having 1 to 6 carbon atoms; and m represents an integer in the range of 0 to 4, provided that, in the case when m is at least 2, each $R^3$ may be the same or different; and n represents an integer in the range of 0 to 5, provided that, in the case when n is at least 2, each $R^4$ may be the same or different; and $Y^5$ represents a leaving group.

* * * * *